United States Patent [19]

Hsieh

[11] Patent Number: 5,696,807

[45] Date of Patent: Dec. 9, 1997

[54] METHODS AND APPARATUS FOR MODULATING X-RAY TUBE CURRENT

[75] Inventor: Jiang Hsieh, Waukesha, Wis.

[73] Assignee: General Electric Company, Milwaukee, Wis.

[21] Appl. No.: 706,613

[22] Filed: Sep. 5, 1996

[51] Int. Cl.⁶ ..................................... H05G 1/34
[52] U.S. Cl. ..................... 378/109; 378/145; 378/110
[58] Field of Search ............................. 378/96, 97, 108, 378/109, 110, 111, 112, 116, 145, 147, 150, 151

[56] References Cited

U.S. PATENT DOCUMENTS

| | | | |
|---|---|---|---|
| 4,454,606 | 6/1984 | Relihan | 378/97 |
| 4,748,649 | 5/1988 | Griesmer et al. | 378/97 |
| 4,942,596 | 7/1990 | Eberhard et al. | 378/112 |
| 5,432,833 | 7/1995 | Coe | 378/112 |

*Primary Examiner*—Don Wong
*Attorney, Agent, or Firm*—John S. Beulick; John H. Pilarski

[57] ABSTRACT

The present invention, in one form, is a system for modulating x-ray tube current as a function of gantry angle and slice location in a computed tomography system. In one embodiment, a desired noise level for a final image is selected, and a desired minimum x-ray photon reading and a desired average x-ray photon reading are identified to produce an image in accordance with the desired noise level. During scanning, actual x-ray photon readings are used with the desired average x-ray photon reading and the desired minimum x-ray photon reading to generate an x-ray modulating factor. This modulating factor is then used to modulate the x-ray tube current.

16 Claims, 2 Drawing Sheets

METHODS AND APPARATUS FOR MODULATING X-RAY TUBE CURRENT

FIELD OF THE INVENTION

This invention relates generally to computed tomography (CT) imaging and more particularly, to modulating x-ray tube current supplied to an x-ray source of a CT imaging system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. An image reconstruction algorithm which may be utilized in reconstructing an image from data obtained in a helical scan is described in U.S. patent application Ser. No. 08/436,176, filed May 9, 1995, and assigned to the present assignee.

Certain scanning parameters, such as x-ray tube current ("mA"), x-ray tube supply voltage ("kV"), slice thickness, scan time, and helical pitch, are known to affect image quality. In addition, the x-ray tube current typically directly relates to the patient x-ray dose. A higher x-ray tube current may, for example, improve the image quality but increase the patient dose. Traditionally, the x-ray tube current is fixed to provide an acceptable image quality and a low patient dose.

With respect to image quality, and as explained above, higher x-ray tube current levels typically produce images with less noise. Conversely, lower x-ray tube current levels are known to cause severe streaking artifacts in the image. This streaking typically results from x-ray photon starvation.

Although higher x-ray tube current levels result in lower noise images, such higher x-ray tube current levels subject a patient to higher x-ray doses and may overload components of the CT system. Particularly, the x-ray tube current setting affects the amount of x-ray flux delivered by the x-ray tube. An x-ray tube typically is limited with respect to the amount of x-ray flux it delivers, without heating, within a fixed period of time. When such limitation is exceeded, the x-ray tube must be cooled to avoid damaging the tube. Therefore, if higher x-ray tube current is used, the scan may have to be interrupted so that the x-ray tube can cool. Higher x-ray tube current levels are also known to cause the CT system data acquisition system (DAS) to overrange, which results in severe shading artifacts.

To reduce patient dose, a system operator may manually vary the x-ray dose. The x-ray dose may be varied both as a function of slice location and projection angle, i.e., the relative angular position of the x-ray source and the object being x-rayed. Typically, the selection of the x-ray dosage depends heavily on the operator's experience. The manual selection of x-ray dosage as a function of slice location is often inaccurate, and both excessive patient dose and insufficient patient dose may occur, even with experienced operators. Moreover, scans of similar objects may not be consistent with different operators conducting such scans.

To more consistently reduce patient dose, it is known to automatically vary the x-ray tube current during a scan as a function of projection angle. One such method is described, for example, in U.S. Pat. No. 5,379,333, entitled "Variable Dose Application By Modulation of X-Ray Tube Current During CT Scanning", which is assigned to the present assignee. This method requires the operator to take two scout images prior to the data acquisition. The two scout images are taken at orthogonal directions and a final x-ray tube current waveform is derived based on the attenuation ratio of the scout images. During a scan, the x-ray tube current is controlled to conform to the predetermined current waveform.

Although this method is effective in reducing the overall tube usage, extra scout images have to be taken. Obtaining the extra scout images is time consuming and cumbersome, and subjects the patient to extra x-ray dose. Further, varying x-ray tube current solely as a function of projection angle may cause excessive doses at the same projection angle of different slice locations within a scan. For example, while scanning a human torso, both the shoulders and lung region are subjected to x-ray doses. At the projection angle and slice location wherein the x-ray tube and the detector align with the orientation of the two shoulder bones, the patient's attenuation characteristics are much higher, thus requiring a high x-ray dose to generate a high quality image. However, when scanning the lung region, i.e., a new slice location, at the same projection angle, such high x-ray dose may be excessive because the lung region has small attenuation characteristics compared to those of the shoulder bones.

It would be desirable to both generate high quality images and reduce patient dose. It also would be desirable to eliminate a need for extra scout images, and to avoid insufficient and/or excessive patient doses for each projection angle and scan location.

SUMMARY OF THE INVENTION

These and other objects may be attained in a system which, in one embodiment, varies the x-ray tube current and the resulting x-ray flux over the duration of the scan to better accommodate different attenuation characteristics between different slices, even at similar view angles. Specifically, in one embodiment, the x-ray tube current is varied, or modulated, as a function of both slice location and projection angle in accordance with a desired noise level in the generated image. In this embodiment, the x-ray tube current is modulated using a scaling factor s defined as:

$$s = \frac{\xi}{\omega_i} f\left(\frac{\epsilon}{\eta_i}\right)$$

where:

$$f(x) = \begin{cases} 1 & \text{if } x \leq 1, \text{ and} \\ x & \text{if } x \geq 1; \text{ and} \end{cases}$$

$\xi$=a desired average photon reading;
$\omega_i$=an actual average photon reading;
$\epsilon$=a desired minimum photon reading; and
$\eta_i$=an actual minimum photon reading.

Prior to performing a scan, an operator selects a desired (or acceptable) noise level for the images to be generated. The desired average photon reading, $\xi$, and the desired minimum photon reading, $\epsilon$, are then determined by the system using the selected noise level. During the scan, actual photon readings, i.e., signal intensities received during the scan, are compared to the desired photon readings to generate scaling factor s. Scaling factor s is multiplied to the x-ray tube current to generate a new current, and the x-ray tube current is adjusted to have a magnitude equal to the magnitude of the new current.

By modulating x-ray tube current in accordance with a desired noise level in the image as described above, image dose is reduced while image quality is maintained. Further, patient dose is reduced, or at least is not excessive, by reducing the x-ray tube current for those projections correlating to lower attenuation characteristics, even at the same projection angles of different slices. In addition, such modulation does not require any additional scout images.

DETAILED DESCRIPTION OF THE DRAWINGS

Figure 1:
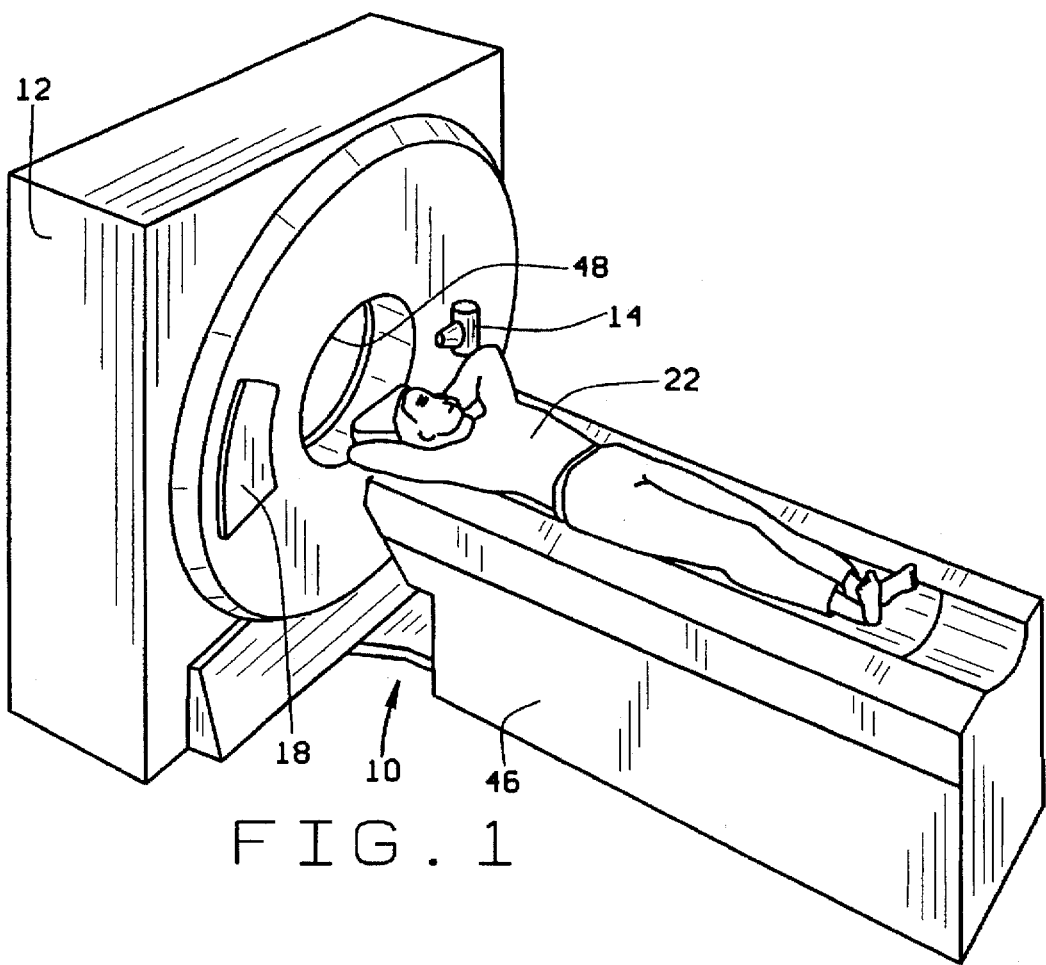
FIG. 1 is a pictorial view of a CT imaging system.
Figure 2:
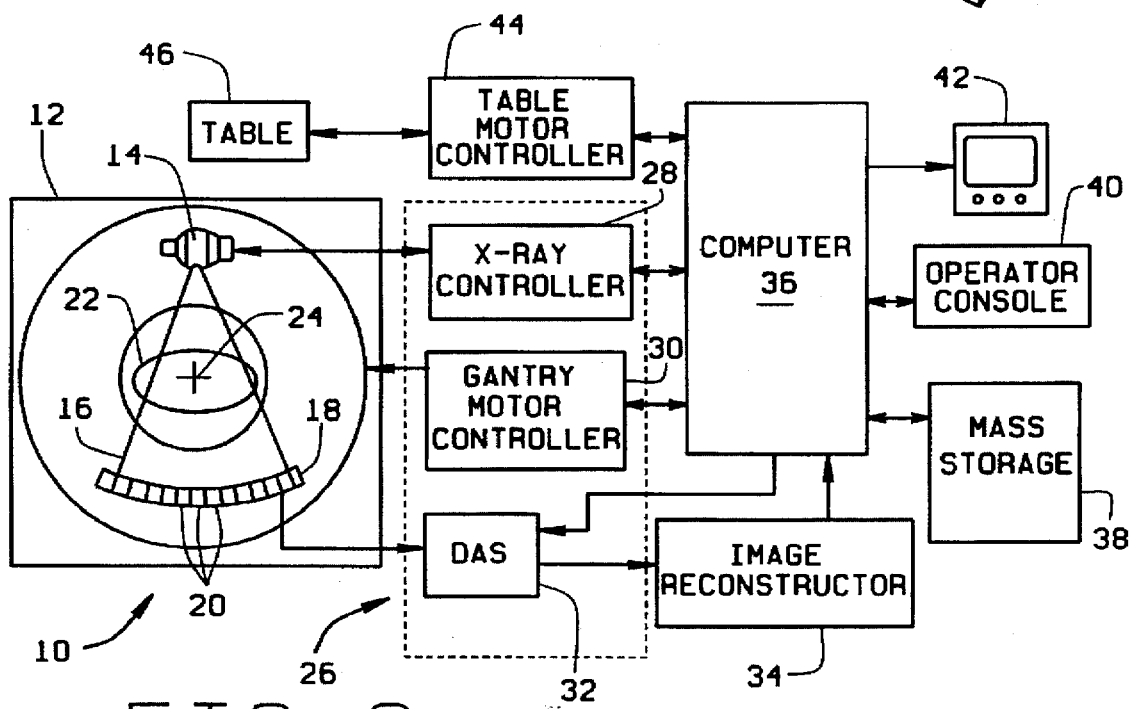
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source, or tube 14 that projects a beam of x-rays 16 along an x-y plane toward a detector array 18 on the opposite side of gantry 12. Detector array 18 is formed by detector elements 20 which together sense the projected x-rays that pass through a medical patient 22. Each detector element 20 produces an electrical signal with a signal level that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The present x-ray tube current modulation is not limited to practice in any particular CT system, nor is such modulation limited to any particular image reconstruction algorithm. Similarly, the present x-ray tube current modulation is not limited to use in connection with any particular scan type such as helical and axial scans. It should be further understood that the current modulation algorithm could be implemented, for example, in computer 36 to control x-ray controller 28 to supply a desired current to x-ray tube 14 (FIG. 2).

In accordance with one embodiment of the present invention, x-ray tube current is modulated based on signal intensities and a selected noise level. With respect to noise levels, and as is known, the variance of a detector element reading, when dominated by quantum noise, is proportional to the measured signal at detector element 20. Specifically:

$$\sigma^2 \alpha \qquad (1)$$

where: $\alpha$ is the measured signal; and
$\sigma$ is the standard deviation of the signal.

To a first order approximation, the variance in the final image scales proportionally to the variance in the measured signal because tomographic reconstruction processes are substantially linear. Therefore, to achieve a desired noise level in the final image, a signal level in the projection may be identified. As described above, signal levels are proportionally related to the attenuation of the beam as it passes through the patient. Therefore, if the attenuation characteristics of the patient are known, then a desired signal level and x-ray current may be used to generate the desired noise level in the final image. However, the patient's attenuation characteristics are not generally known prior to a scan. With known methods, the patient's attenuation characteristics are "guessed" by a system operator, or the operator performs scout scans to determine the patient's attenuation characteristics.

In a helical scan, the x-ray tube and the detector rotate at a substantially constant speed about the patient. The gantry translates one helical pitch in each gantry rotation. Helical pitch is the ratio of the table movement in one rotation of the x-ray source to the slice width defined by a source collimator. Generally, when using a helical pitch of 1:1, the patient's anatomy remains substantially constant between rotations, or slices. Particularly, attenuation characteristics in a first rotation, or slice, will be substantially similar to attenuation characteristics in a second, subsequent rotation, or slice. Similarly, attenuation characteristics of the patient do not change quickly as a function of the projection angle. Specifically, attenuation characteristics at a first projection angle are substantially similar to attenuation characteristics at a second projection angle near the first projection angle.

In accordance with one embodiment of the present invention, the x-ray tube current is dynamically modified in accordance with measured attenuation characteristics. Particularly, in the one embodiment, measured attenuation characteristics, i.e., x-ray photon readings, are utilized to generate an x-ray tube current scaling factor, s, which is used to modulate the x-ray tube current. More specifically, x-ray flux data such as average x-ray photon readings and minimum x-ray photon readings are obtained from detector 18 and are used to generate scaling factor, s, and thus modulate the x-ray tube current.

Figure 3:
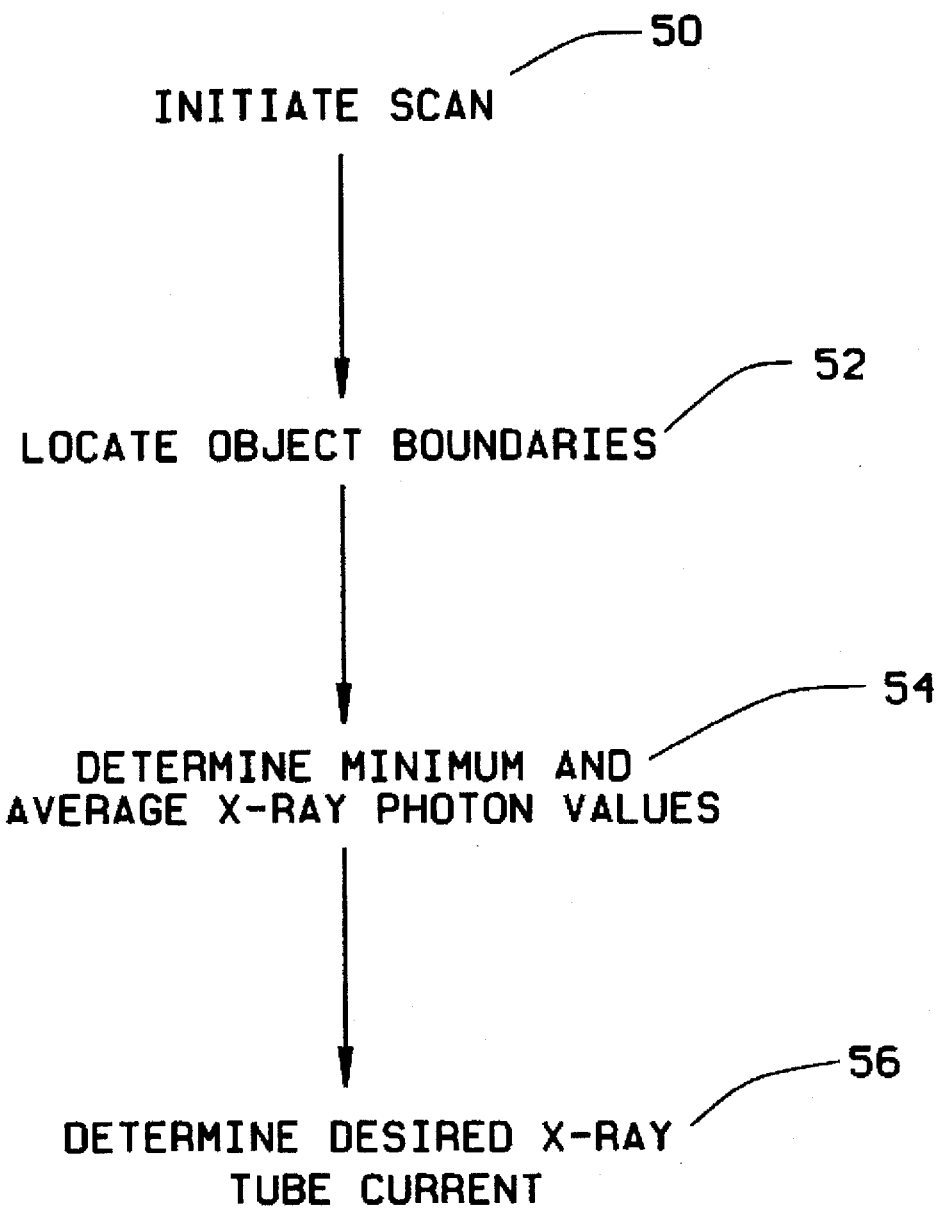
FIG. 3 illustrates a sequence of steps executed in a scan in accordance with one embodiment of the present invention.

FIG. 3 illustrates a sequence of steps executed in accordance with one embodiment of the present invention to modulate x-ray tube current. Specifically, after initiating a scan 50, boundaries of the object of interest are located 52. The location of the boundaries affects the accuracy of the average photon readings of the object over channels 20 of detector 18. For example, if the boundaries are not located, and if the scanned object is narrow in the y dimension and wide in the x dimension, only a few detector elements 20, or channels, will receive attenuated signals when x-ray tube 14 and detector 18 are aligned with the x axis of the x-y plane. Conversely, a majority of channels 20 are exposed directly to x-ray source 14 without object attenuation. Therefore, an average photon reading of all detector channels 20 will be high, thus causing an over-estimation. Boundaries, therefore, are identified and utilized to reduce such over-estimations. The boundaries may be located by known means, such as, for example, a simple threshold method.

Once the boundaries are located, the x-ray flux values are determined. In this embodiment, minimum and average x-ray photon values within the boundaries of the object are determined 54. Simple box car smooth filtering, as is known, may be utilized to reduce the influence of photon noise. The minimum and average photon values may be determined with reference to only a fraction of channels 20 within the located boundaries. For example, the minimum and average photon values may be calculated using every second, third, fourth, or even nth, channel 20 of detector array 18.

Using the above described x-ray flux values, a desired x-ray tube current is then determined 56. Specifically, a mapping function is utilized to identify a desired x-ray tube current reading. In one embodiment, the mapping function is used to produce a desired x-ray tube current reading in accordance with a desired (or acceptable) noise level. The noise level may be a default image quality index for a particular type of study, a set of recommended parameters, the system operator's choice, or any other input. The desired noise level establishes the basis for the x-ray exposure. Particularly, for the desired noise level, a desired average x-ray photon reading, $\xi$, needed to obtain the image quality may be calculated in accordance with Equation (1). Similarly, a desired minimum x-ray photon reading, $\epsilon$, that will ensure streak free images with the prescribed noise level may be calculated in accordance with Equation (1). The minimum x-ray photon reading, $\epsilon$, and the average x-ray photon reading, $\xi$, may be stored in a memory of computer 36.

Using the mapping function, a scaling factor, s, is generated by comparing the desired average photon reading, $\xi$, and the desired minimum photon reading, $\epsilon$, with an actual obtained average photon reading, $\omega_i$, and an actual minimum photon reading, $\eta_i$. Scaling factor, s, is used to modulate the x-ray tube current and adjust the x-ray tube current to a new x-ray tube current so that the actual x-ray flux more closely corresponds to the desired x-ray flux. For example, the scaling factor can be expressed as:

$$s = \frac{\xi}{\omega_i} f\left(\frac{\epsilon}{\eta_i}\right) \quad (2)$$

where:

$$f(x) = \begin{cases} 1 & \text{if } x \leq 1, \text{ and} \\ x & \text{if } x \geq 1; \text{ and} \end{cases} \quad (3)$$

$\xi$=the desired average photon reading;
$\omega_i$=the actual average photon reading;
$\epsilon$=the desired minimum photon reading; and
$\eta_i$=the actual minimum photon reading.

The modified x-ray tube current may be determined using the following:

modified x-ray tube current=s * supplied x-ray tube current, (4)

where supplied x-ray tube current is the current supplied by x-ray controller 28 to x-ray source 14. To achieve such modulation, computer 36 may output an x-ray tube current adjustment command to x-ray controller 28. Accordingly, the x-ray tube current is modulated during scanning as a function of slice location and gantry angle.

Scaling factor s may be generated after each measurement and stored in the memory of computer 36. However, scaling factor s may be generated less often, i.e., once every N slice or once every x degrees of gantry rotation. In addition, to reduce stringent timing requirements for the x-ray tube current adjustment, a scaling factor derived from the previous slice can be used for the current adjustment in connection with the present slice. Therefore, the system has more than one second to determine and preform the desired adjustment.

X-ray tube current is also modulated to minimize DAS overrange. Particularly, as is known, DAS 32 has a dynamic range which, if exceeded, causes severe shading artifacts in the generated image. DAS dynamic range is related directly to the flux generated by the x-ray tube current. To identify DAS overrange, a maximum photon reading of entire detector 18 is determined. Scaling factor, s, is multiplied to the maximum photon reading to generate a scaled DAS maximum value. If scaled maximum DAS value exceeds the dynamic range of DAS 32, scaling factor, s, is reduced to prevent the modified x-ray tube current from causing DAS overrange. Particularly, scaling factor, s, is reduced before modulating the x-ray tube current in accordance with Equation (4).

Similarly, the number of channels 20 in overrange conditions may be identified. If a large number of channels 20 are in overrange condition, then the reconstructed image may have shading artifact related to the overrange. Therefore, scaling factor s is reduced to reduce channel overrange.

In many cases, DAS overrange and under-range might happen in the same view. For example, if a large patient 22 is scanned off-centered in the shoulder region, some channels 20 exposed directly to x-ray source 14 will experience overrange, while other channels 20 blocked by the patient's shoulder bones will experience under-range. Under this condition, a compromise may be made to ensure the overall best image quality. For example, the overrange requirement may be relaxed. To relax the overrange requirement, and rather than having no overrange channel, m overrange channels could be acceptable. If the number of overranged channels is small, it is believed that image artifacts are not severe. Therefore, scaling factor s can be selected to have the highest value that will produce no more than m overranged channels in a projection view.

The above described modulation is believed to provide a significant reduction in x-ray dose while maintaining the overall image quality. Further, x-ray current is dynamically modified as a function of slice and projection angle. Additionally, reliance on operator experience is reduced, thus producing more consistent image quality. Furthermore, no additional scout images are required to modulate the x-ray tube current.

As described above, the x-ray flux parameters of average and minimum x-ray photon values are used in connection with x-ray tube modulation. Other x-ray flux parameters, such as the shape of the flux waveform or the flux standard deviation, could similarly be utilized for such modulation. In addition, rather than modulating x-ray tube current, the x-ray flux can be used to control the collimator aperture size of the x-ray source collimator and to control the x-ray tube voltage. For example, an operator might select a slice thickness that is too thin, causing x-ray photon starvation. Using the flux information as described above, the system could generate a warning for the operator or dynamically change the collimator aperture as needed during the scan.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Accordingly, the spirit and scope of the invention are to be limited only by the terms of the appended claims.

What is claimed is:

1. A method for modulating x-ray tube current supplied to an x-ray source of an imaging system, the imaging system using attenuation data received by detector cells to reconstruct an image of an object scanned by the system, said method comprising the steps of:

monitoring at least one x-ray tube flux parameter;

generating an x-ray tube current scaling factor based on the monitored x-ray tube flux parameter, said generated x-ray tube current scaling factor s being:

$$s = \frac{\xi}{\omega_i} f\left(\frac{\epsilon}{\eta_i}\right)$$

where:

$$f(x) = \begin{cases} 1 & \text{if } x \leq 1, \text{ and} \\ x & \text{if } x \geq 1; \text{ and} \end{cases}$$

$\xi$=the desired average photon reading;
$\omega_i$=an actual average photon reading;
$\epsilon$=the desired minimum photon reading; and
$\eta_i$=an actual minimum photon reading; and modulating the x-ray tube current using the generated x-ray tube current scaling factor.

2. A method in accordance with claim 1 wherein monitoring at least one x-ray tube flux parameter comprises the step of determining at least one of a minimum x-ray photon value and an average x-ray photon value.

3. A method in accordance with claim 1 wherein the imaging system further includes a data acquisition system, and said method further comprises the steps of:

identifying a data acquisition system overrange; and modulating the x-ray tube current using said identified data acquisition system overrange.

4. A method in accordance with claim 1 wherein the imaging system further includes a computer having a memory, and said method further comprises the step of storing the desired minimum x-ray photon reading and the desired average x-ray photon reading in the computer memory.

5. A method in accordance with claim 4 further comprising the step of storing said x-ray tube current scaling factor in the computer memory.

6. A system for modulating x-ray tube current supplied to an x-ray source of an imaging system, said modulating system configured to:

monitor at least one x-ray tube flux parameter;

generate an x-ray tube current scaling factor based on the monitored x-ray tube flux parameter, said generated x-ray tube current scaling factor s being:

$$s = \frac{\xi}{\omega_i} f\left(\frac{\epsilon}{\eta_i}\right)$$

where:

$$f(x) = \begin{cases} 1 & \text{if } x \leq 1, \text{ and} \\ x & \text{if } x \geq 1; \text{ and} \end{cases}$$

$\xi$=the desired average photon reading;
$\omega_i$=an actual average photon reading;
$\epsilon$=the desired minimum photon reading; and $\eta_i$=an actual minimum photon reading; and modulate the x-ray tube current using the generated x-ray tube current scaling factor.

7. A system in accordance with claim 6 wherein to monitor at least one x-ray tube flux parameter, said system is configured to determine at least one of a minimum x-ray photon value and an average x-ray photon value.

8. A system in accordance with claim 6, wherein the imaging system further includes a data acquisition system, and said system is further configured to:

identify a data acquisition system overrange; and modulate the x-ray tube current using said identified data acquisition system overrange.

9. A system in accordance with claim 6 wherein the imaging system further includes a computer having a memory, and said system is further configured to store the desired minimum x-ray photon reading and the desired average x-ray photon reading in the computer memory.

10. A system in accordance with claim 9 further configured to store said x-ray tube current scaling factor in the computer memory.

11. A system for dynamically adjusting at least one component in a computed tomography imaging system, the imaging system including an x-ray source having a collimator with an aperture, said dynamic adjusting system configured to:

determine boundaries of an object to be imaged;

monitor at least one x-ray tube flux parameter, including at least one of a minimum x-ray photon value and an average x-ray photon value, within the determined boundaries;

identify an adjustment to be made to the imaging system component based on the monitored x-ray tube flux parameter; and cause the parameter to be adjusted based on the identified adjustment.

12. A system in accordance with claim 11 wherein the component to be dynamically adjusted is the x-ray source collimator aperture.

13. A system in accordance with claim 11 wherein the component to be dynamically adjusted is the voltage supplied to the x-ray source.

14. A system in accordance with claim 11 wherein the component to be dynamically adjusted in the x-ray source current.

15. A system in accordance with claim 11 wherein to monitor at least one x-ray tube flux parameter, said system is configured to monitor the x-ray flux waveform.

16. A system in accordance with claim 11 wherein to monitor at least one x-ray tube flux parameter, said system is configured to monitor the x-ray flux standard deviation.

* * * * *